(12) United States Patent
Lerch et al.

(10) Patent No.: US 10,321,880 B2
(45) Date of Patent: Jun. 18, 2019

(54) MEDICAL IMAGING DEVICE HAVING A FRAME ELEMENT FOR DISPOSING A COMPONENT

(71) Applicant: Siemens Aktiengesellschaft, Munich (DE)

(72) Inventors: Daniel Lerch, Weilersbach (DE); Carsten Thierfelder, Pinzberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 779 days.

(21) Appl. No.: 14/956,421

(22) Filed: Dec. 2, 2015

(65) Prior Publication Data
US 2016/0174914 A1 Jun. 23, 2016

(30) Foreign Application Priority Data
Dec. 18, 2014 (DE) .................... 10 2014 226 467

(51) Int. Cl.
*A61B 6/00* (2006.01)
*A61B 6/04* (2006.01)
(Continued)

(52) U.S. Cl.
CPC .......... *A61B 6/0407* (2013.01); *A61B 5/0555* (2013.01); *A61B 6/032* (2013.01);
(Continued)

(58) Field of Classification Search
CPC ....... A61B 6/0407; A61B 6/467; A61B 6/462; A61B 6/032; A61B 5/0555; A61B 6/08; A61B 6/037
(Continued)

(56) References Cited

U.S. PATENT DOCUMENTS 5,523,571 A * 6/1996 Velazquez .............. A61B 6/037
250/363.05
6,031,888 A * 2/2000 Ivan ...................... A61B 6/4441
378/196
(Continued)

FOREIGN PATENT DOCUMENTS

CN 101102813 A 1/2008
CN 102164636 A 8/2011
(Continued)

OTHER PUBLICATIONS

Korean Office Action dated Dec. 11, 2016.
(Continued)

*Primary Examiner* — Sanjay Cattungal
(74) *Attorney, Agent, or Firm* — Harness, Dickey & Pierce, P.L.C.

(57) ABSTRACT

A medical imaging device is disclosed. In an embodiment, the medical imaging device includes an imaging area; a patient positioning device including a positioning table and a transfer plate for positioning a patient in a patient positioning area; a frame element for disposing at least one component relative to the imaging area and/or the patient positioning device, wherein the frame element has a first side arm, a second side arm and an apex area disposed between the first side arm and the second side arm; and a first mounting device and a second mounting device for retaining the frame element. The apex area is disposed above the transfer plate in respect of a vertical direction.

17 Claims, 7 Drawing Sheets

(51) Int. Cl.
*A61B 5/055* (2006.01)
*A61B 6/03* (2006.01)
*A61B 6/08* (2006.01)

(52) U.S. Cl.
CPC .............. *A61B 6/462* (2013.01); *A61B 6/467* (2013.01); *A61B 6/037* (2013.01); *A61B 6/08* (2013.01)

(58) Field of Classification Search
USPC ................................................. 600/407–480
See application file for complete search history.

(56) References Cited

U.S. PATENT DOCUMENTS

| | | | |
|---|---|---|---|
| 6,304,627 B1* | 10/2001 | Horbaschek | A61B 6/00 324/318 |
| 6,442,230 B1 | 8/2002 | Wilting et al. | |
| 6,490,477 B1* | 12/2002 | Zylka | A61B 6/04 600/414 |
| 6,665,554 B1 | 12/2003 | Charles et al. | |
| 9,247,917 B2* | 2/2016 | Kodaira | A61B 6/032 |
| 9,974,496 B2* | 5/2018 | Liu | A61G 13/04 |
| 10,013,759 B2* | 7/2018 | Allmendinger | G06T 7/0012 |
| 10,172,574 B2* | 1/2019 | Schafer | A61B 6/02 |
| 2006/0214097 A1* | 9/2006 | Wang | G01T 1/1611 250/252.1 |
| 2009/0304153 A1 | 12/2009 | Amelia et al. | |
| 2010/0027744 A1* | 2/2010 | Brown | A61N 5/1084 378/65 |

FOREIGN PATENT DOCUMENTS

| | | |
|---|---|---|
| DE | 10 2014 215 953 A1 | 2/2016 |
| JP | 2002511015 A | 4/2002 |
| JP | 2002538874 A | 11/2002 |
| JP | 2008522677 A | 7/2008 |

OTHER PUBLICATIONS

German Office Action dated Jul. 31, 2015.
Korean Notice of Allowance dated Apr. 13, 2017.
Chinese Office Action and English translation thereof dated Mar. 30, 2018.

* cited by examiner

MEDICAL IMAGING DEVICE HAVING A FRAME ELEMENT FOR DISPOSING A COMPONENT

PRIORITY STATEMENT

The present application hereby claims priority under 35 U.S.C. § 119 to German patent application number DE 102014226467.7 filed Dec. 18, 2014, the entire contents of which are hereby incorporated herein by reference.

FIELD

At least one embodiment of the invention generally relates to a medical imaging device, having an imaging area; a patient positioning device comprising a positioning table and transfer plate for positioning a patient in a patient positioning area; and/or a frame element for disposing at least one component relative to the imaging area and/or the patient positioning device.

BACKGROUND

To improve workflow on medical imaging devices, in particular on large imaging machines such as computed tomography scanners, PET/CT scanners, SPECT/CT scanners, magnetic resonance tomography scanners and similar, components such as e.g. a camera, in particular an optical camera, will be increasingly used for patient monitoring or display devices which provide the patient with visual information or show film sequences.

To obtain an image of a region of interest of the patient, the patient is positioned on the transfer plate and moved together with the transfer plate into an imaging area of the medical imaging device such that the region of interest of the patient is disposed in the imaging area. The imaging area can be covered at least from above. In particular, the imaging area can be formed by a tunnel-like aperture. This places significant requirements on the disposition of the components.

For example, a camera is designed to optically capture a patient, both when the latter is still positioned in front of the imaging area and also when the patient has been moved somewhat further into the imaging area. Conversely, the patient must be able to see a display device from the recumbent position both when the patient's head is in front of the imaging area and also when it is in the imaging area.

The particular disadvantage of installing these components in the conventional manner on a wall or ceiling of the examination room in which the medical imaging device is disposed is the large amount of space required for installation and the increased cable lengths, as it is necessary to run cables for data and/or power transmission from and to the components through the floor and wall up to the ceiling.

Alternative mounting facilities for the display device are disposed directly at the head end of the transfer plate, which, however, likewise has two disadvantages, namely that they can only be used there for "head-first" positioned patients and that they are an obstacle to examinations in the head area of the patient, i.e. they would have to be mounted and dismounted depending on the clinical application.

It is also known to dispose microphones and loudspeakers in the imaging area, in particular in the tunnel-like aperture, for communication between the patient and a medical imaging device user. The problem here is that microphones which are optimized for the direction profile of the patient located in the imaging area are inadequately suitable for communication with a patient or user located in front of the imaging area, and microphones having a less target-oriented characteristic are more prone to interference. Therefore, in a conventional medical imaging device, additional microphones are required for improved communication with a patient or user located in front of the imaging area.

Modern systems for planning needle paths for interventions (hereinafter referred to as laser-based intervention systems) generally use lasers which indicate the point of insertion and/or insertion direction. Laser systems are also used in radiation therapy planning in order to enable particular slice planes or points on the patient to be marked. A projection device of this kind must be disposed such that the laser can be projected onto the patient as unobstuctedly as possible. The projection device must allow highly precise marking at a predefined distance in front of the imaging area. For example, in the case of a computed tomography scanner, marking parallel to the scanning plane may be required. For this purpose, projection devices are known which are mounted on the wall of the examination room, which means that additional installation work is required.

SUMMARY

At least one embodiment of the invention enables at least one component to be better disposed relative to an imaging area and/or a patient positioning device of a medical imaging device.

At least one embodiment is directed to the medical imaging device. Further advantageous features of the invention are contained in the sub-claims.

In particular, at least one embodiment of the invention relates to a medical imaging device, comprising
  an imaging area,
  a patient positioning device comprising a positioning table and a transfer plate for positioning a patient in a patient positioning area,
  a frame element for disposing at least one component relative to the imaging area and/or the patient positioning device, wherein the frame element has a first side arm, a second side arm and an apex area disposed between the first side arm and the second side arm, and
  a first mounting device and a second mounting device for retaining the frame element,
  wherein the apex area is disposed vertically above the transfer plate.

BRIEF DESCRIPTION OF THE DRAWINGS

The invention will now be explained in greater detail once again with reference to the accompanying drawings using example embodiments. The representation in the drawings is schematic and greatly simplified, and not necessarily to scale.

In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In particular, at least one embodiment of the invention relates to a medical imaging device, comprising
 an imaging area,
 a patient positioning device comprising a positioning table and a transfer plate for positioning a patient in a patient positioning area,
 a frame element for disposing at least one component relative to the imaging area and/or the patient positioning device, wherein the frame element has a first side arm, a second side arm and an apex area disposed between the first side arm and the second side arm, and
 a first mounting device and a second mounting device for retaining the frame element,
 wherein the apex area is disposed vertically above the transfer plate.

According to a preferred aspect of at least one embodiment of the invention, the imaging area is formed by a tunnel-like aperture.

According to a preferred aspect of at least one embodiment of the invention, the transfer plate is disposed on the positioning table in a movable manner relative to the positioning table in such a way that the transfer plate can be moved into the imaging area in a longitudinal direction of the transfer plate.

According to a preferred aspect of at least one embodiment of the invention, the first and the second mounting device are disposed mutually offset in respect of a transverse direction which is horizontal and at right angles to the longitudinal direction.

According to a preferred aspect of at least one embodiment of the invention, the frame element is retained between the first mounting device and the second mounting device such that the first side arm is disposed between the apex area and the first mounting device, and the second side arm is disposed between the apex area and the second mounting device.

According to a preferred aspect of at least one embodiment of the invention, the apex area is disposed in a region defined by the transfer plate in respect of the transverse direction.

According to a preferred aspect of at least one embodiment of the invention, the apex area is disposed above the patient positioning area in respect of the vertical direction.

According to a preferred aspect of at least one embodiment of the invention, at least one section of the first side arm and at least one section of the second side arm are disposed between the apex area and the imaging area in respect of the longitudinal direction.

According to a preferred aspect of at least one embodiment of the invention, the at least one component is an element from the group comprising a camera, a projection device, an illumination device, a display device, an input device, an output device, a microphone, a loudspeaker, an interface for transmitting data and/or power, a rail guide, a support arm, and combinations thereof. In addition, the at least one component can have, for example, an infusion bag, a partition plate, in particular for shielding against ionizing radiation, or similar.

According to at least one embodiment of the invention, the first side arm and the second side arm are therefore used to implement an extension of the frame element in both the transverse direction and the longitudinal direction. A frame element having a high degree of strength and a high degree of rigidity can be implemented in this way. The at least one component can therefore be disposed in a constructionally simple manner in different positions relative to the imaging area and/or the patient positioning device with a high degree of mechanical stability.

In particular, the apex area can be retained so as to project from the first side arm and the second side arm along the longitudinal direction. The position of the apex area can in particular be optimized in respect of the optical and acoustic conditions both for a patient positioned in an offset manner in the longitudinal direction in front of the imaging area and for a patient who has been moved into the imaging area. This can be achieved in particular by selecting appropriate inclinations relative to the horizontal plane and extensions and curvatures of the first side arm and the second side arm.

In particular, the apex area can be disposed offset to the transfer plate in respect of the longitudinal direction. In addition, the first mounting device and the second mounting device can be mutually offset in respect of the longitudinal direction and/or in respect of the vertical direction.

The patient positioning area is a spatial area for positioning the patient. In particular, the patient positioning area can be vertically adjacent to the patient positioning device, e.g. to the couch, plate or similar. In particular, the patient positioning area can be defined spatially at least partially by the patient positioning device and/or a patient positioned recumbently on the patient positioning device. In particular, the patient can be positioned recumbently in at least part of the patient positioning area.

According to a preferred aspect of at least one embodiment of the invention, the first side arm is disposed to the left of the patient positioning area and/or the second side arm is disposed to the right of the patient positioning area in respect of the transverse direction. The left-hand and the right-hand side are definable with respect to a vertical plane running through the patient positioning area in the longitudinal direction. The at least one component can therefore be disposed to the left and/or right of the patient in a constructionally simple manner with a high degree of mechanical stability. The first mounting device and/or the second mounting device can disposed in an area defined by the imaging area in respect of the longitudinal direction.

According to a preferred aspect of at least one embodiment of the invention, the first mounting device is disposed to the left of the patient positioning area and/or the second mounting device to the right of the patient positioning area in respect of the transverse direction. In particular, the first mounting device can be disposed to the left of the imaging area and/or the second mounting device to the right of the imaging area in respect of the transverse direction. A frame element with an increased extension in the transverse direction can be implemented with a high degree of strength and rigidity in this manner.

According to a preferred aspect of at least one embodiment of the invention, the first side arm, the second side arm and the apex area together form a U-shaped section of the frame element. In particular, the frame element can be of curved design. A frame element having a high degree of strength and a high degree of rigidity can therefore be implemented in a constructionally simple manner.

According to a preferred aspect of at least one embodiment of the invention, the medical imaging device has a gantry, wherein the first mounting device and/or the second mounting device are disposed on the gantry. The gantry forms a supporting structure of the medical imaging device. In particular, the gantry is suitable for absorbing forces and torques applied to the medical imaging device and for transmitting them to a structural support. The structural support can be e.g. a floor, in particular a floor plate, a wall or a ceiling of the examination room.

In this way the gantry can also absorb forces and torques applied to the frame element and transmit them to the structural support. This obviates the need for additional supporting structures for connecting the frame element to a structural support, in particular a ceiling or a wall. This significantly reduces the installation work for a medical imaging device.

In addition, this reduces the dependence of the functionality of the at least one component on the conditions present in the examination room, in particular on the position and quality of a structural support. In particular, the orientation and position of the at least one component can be fully adjusted and monitored by parts of the medical imaging device. This simplifies the installation and maintenance work involved, in particular for remote maintenance, as well as the processing of customer requests and service orders.

In a preferred embodiment of the invention, installation work in the examination room is reduced to the orientation of the gantry and the patient positioning device relative to one another. The medical imaging device can in particular have a partition plate for shielding against ionizing radiation. This additionally reduces the structural requirements placed on the examination room.

In particular, cables which can transmit data and/or power to and from the at least one component can be run from the gantry to the frame element. Extended cable runs, particularly compared to an arrangement of components and/or interfaces on the patient positioning device, and/or moving cable runs are therefore avoided, thereby reducing the costs.

In particular, the first mounting device can be disposed on a left-hand side of the gantry and the second mounting device on a right-hand side of the gantry. The frame element can therefore extend from the left-hand side of the gantry to the right-hand side of the gantry and can be supported by the left-hand and right-hand side of the gantry. In particular, the frame element and the gantry can have a stabilizing and/or reinforcing effect on one another. Firm fixation of the frame element in the first mounting device and the second mounting device provides a particularly large stabilizing and/or reinforcing effect.

The first mounting device and/or the second mounting device can each have support device. The support device can be suitable for absorbing forces and torques applied to the frame element and transmitting them to a structural support. The support device need not necessarily be connected to a gantry. A gantry-independent support of the frame element can therefore be implemented in this manner.

According to a preferred aspect of at least one embodiment of the invention, at least one section of the first side arm and at least one section of the second side arm are disposed between the apex area and the gantry in respect of the longitudinal direction.

According to a preferred aspect of at least one embodiment of the invention, the gantry has a stationary support frame and a tilting frame mounted in a tiltable manner on the stationary support frame. In particular, the tilting frame can be tiltable about a tilting axis essentially parallel to the transverse direction.

According to a preferred aspect of at least one embodiment of the invention, the first mounting device and/or the second mounting device are disposed on the stationary support frame. This enables a mechanically particularly stable arrangement of the at least one component to be implemented. In particular, it prevents the at least one component from moving in conjunction with the tilting movement of the tilting frame. The frame element can be disposed on the stationary support frame such that any collision of the tilting frame with the frame element is prevented.

According to a preferred aspect of at least one embodiment of the invention, the first mounting device and/or the second mounting device are disposed on the tilting frame.

According to a preferred aspect of at least one embodiment of the invention, the apex area is disposed approximately at the height of an upper edge of the gantry in respect of the vertical direction. The apex area can be disposed above or below the upper edge of the gantry in respect of the vertical direction. Preferably the distance from the apex area to the upper edge of the gantry is less than 0.6 meters, with particular preference less than 0.3 meters, in respect of the vertical direction.

According to a preferred aspect of at least one embodiment of the invention, the frame element and the gantry together form a circumferentially closed shape. The circumferentially closed shape has high strength and rigidity. This makes it possible to implement the disposition of the at least one component in a mechanically particularly stable manner.

According to a preferred aspect of at least one embodiment of the invention, the frame element is movably retained between the first mounting device and the second mounting device such that the position of the apex area is adjustable in respect of the longitudinal direction and/or in respect of the vertical direction. In particular, the frame element can be retained in a swiveling manner between the first and the second mounting device. In this way the disposition of the at least one component, e.g. a camera or a display device, can be adjusted relative to the patient. This adjustment can take place according to the needs of the patient and/or user. The adjustment can also take place according to the examination requirements.

In particular, the frame element can be retained in a swiveling manner between the first and the second mounting device from a front area to a rear area of the medical imaging device. The front and rear area are definable with respect to a vertical plane running through the imaging area in the transverse direction. The positioning table is disposed in front of the imaging area in respect of the longitudinal direction. The apex area can therefore be disposed both in front of and behind the imaging area in respect of the longitudinal direction. In particular, the at least one component, e.g. a camera or a display device, can be disposed with a field of view onto a patient whose head is behind the gantry, and/or in a field of vision of that patient.

According to a preferred aspect of at least one embodiment of the invention, the frame element has a device for positioning the at least one component along the frame element. In particular, connecting elements, e.g. hooks or recesses, can be provided at predetermined positions along the frame element for e.g. form-fit and/or detachable connection to the at least one component. The at least one component can have a component-side connecting element designed to correspond to the connecting element. A rail guide incorporated in the frame element can also be provided for positioning at least one component along the frame element.

According to a preferred aspect of at least one embodiment of the invention, there is disposed on the frame element at least one support arm for disposing the at least one component. In particular, the support arm can be rotatably and/or swivelably disposed on the frame element relative the frame element. In addition, the support arm can be positionable along the frame element, e.g. by way of the rail guide. The support arm can optionally have one or more telescopic devices.

In particular, the at least one component can be disposed, by way of the support arm and/or the device for positioning, in an area facing away from the imaging area in respect of the partition plate for shielding against ionizing radiation.

According to a preferred aspect of at least one embodiment of the invention, at least one camera is disposed on the apex area such that the imaging area and/or the patient positioning area can be optically captured at least partially by the camera. This is achieved by selecting a disposition of the apex area relative to the imaging area and/or to the patient positioning area according to the camera's field of view. This enables the patient to be optically captured both when the patient is positioned on the transfer plate in front of or behind the medical imaging device and when the patient has been moved into the imaging area. To improve the view into the imaging area, the camera can be disposed so as to rotate relative to the frame element e.g. about an axis parallel to the transverse direction. In particular, this enables regions of the patient which are disposed in the imaging area and/or to the rear of the medical imaging device to be optically captured.

According to a preferred aspect of at least one embodiment of the invention, a display device is disposed in the apex area such that the display device is viewable from at least part of the imaging area and/or at least part of the patient positioning area. This is achieved by selecting a disposition of the apex area relative to the imaging area and/or the patient positioning area according to the patient's viewing conditions. This enables the monitor to be viewed by the patient both when the patient is positioned on the transfer plate in front of or behind the medical imaging device and when the patient has been moved into the imaging area. The display device can be e.g. a monitor, a screen, an LCD display and similar. To improve the visibility of the display device for the patient, the display device can be disposed so as to rotate relative to the frame element about another axis parallel to the transverse direction.

According to a preferred aspect of at least one embodiment of the invention, an input and/or output device connected to a control device of the medical imaging device is disposed on the frame element. This connection can be hard-wired or wireless. The input and/or output device can be disposed in particular rotatably on a support arm which is positionable e.g. along the frame element. The input and/or output device can have a touchpad and/or control buttons, for example.

According to a preferred aspect of at least one embodiment of the invention, at least one microphone and/or at least one loudspeaker are disposed on the frame element. In particular, the at least one microphone and the at least one loudspeaker are disposed on the apex area and/or the first and the second side arm such that the corresponding pickup or output characteristic, as the case may be, is suitable both for communication with a patient who has been moved into the imaging area and with a patient positioned in front of the imaging area and/or a user located in front of the imaging area.

In particular, a microphone can be disposed on the apex area. In the case of a patient positioned supine on the transfer plate, the microphone is therefore facing the patient's mouth. In particular, a first loudspeaker can be disposed on the first side arm and/or a second loudspeaker on the second side arm. For the patient positioned supine on the transfer plate, the first and/or the second loudspeaker are therefore each facing a patient's ear. Improved acoustic communication with the patient can be implemented in this way. In particular, it would be conceivable for the at least one microphone and the at least one loudspeaker to be used for communication of the patient and/or of the user located in front of the imaging area with medical or technical personnel present at a remote location.

According to a preferred aspect of at least one embodiment of the invention, at least one interface for transmitting data and/or power is disposed on the frame element. In particular, the at least one interface can be designed for connection to the at least one component, a data and/or power transmission network, a power consuming and/or data processing device and the like. The power consuming and/or data processing device can be in particular an injection device or a physiological monitoring device. The physiological monitoring device can be, for example, an electrocardiograph (ECG), a respiration monitoring device (Pulmo), a pulse oximeter or the like. In particular, the at least one interface can be implemented as a connection to the electrical power supply of the at least one component and/or of the power consuming and/or data processing device. In particular, cables for transmitting data and/or power can be incorporated into the frame element. This avoids having addition cable runs, thereby reducing installation work and the failure proneness of the medical imaging device. In particular, moving cable runs are avoided and therefore costs reduced compared to having the interfaces disposed in the transfer plate.

According to a preferred aspect of at least one embodiment of the invention, a projection device for projecting light into the imaging area and/or into the patient positioning area is disposed on the frame element. In particular, the projection device can have a plurality of projection elements. The projection elements can be disposed at intervals in the longitudinal direction and/or in the transverse direction on the frame element. The solid angle range from which light, for example, can be projected onto the patient and/or parts of the medical imaging device is therefore increased. This reduces shadowing effects. The area onto which light is projected is therefore increased. In particular, the area onto which light is projected can include parts of the left-hand side and/or right-hand side of the patient. By projecting light onto the patient and/or parts of the medical imaging device, functional illumination, in particular for illuminating areas, for example, can be implemented. For example, this makes it easier to perform interventions in the area, in particular the placement of needle paths and/or cannulas.

Rigid fixation of the frame element, e.g. on the stationary part of the gantry, enables the mechanical stability of the projection device to be increased. Light can therefore be projected very precisely onto the patient and/or parts of the medical imaging device. For example, image information can thus be projected very precisely onto the patient, in particular onto the patient's skin, and/or onto the transfer plate. This image information can be, for example, slice planes, the position of organs, particularly veins, an entry direction, the position of regions to be imaged or imageable by the medical imaging device, and the like. In particular, the light can be a laser. A particularly high projection accuracy can therefore be achieved.

According to a preferred aspect of at least one embodiment of the invention, the medical imaging device has a laser-based intervention system, wherein the laser-based intervention system incorporates the projection device. The laser-based intervention system can also have a projection control unit for controlling the projection device. The projection device can be wirelessly linked or hard-wired to the projection control unit of the laser-based intervention system. For a laser-based intervention system, mounting of the projection device on the frame element is particularly advantageous, as laser beams can be projected from there onto a large area of the patient positioned on the transfer plate, in particular onto the patient's left and right side. It would likewise be conceivable for the projection device to be part of a laser system for radiation therapy planning (RTP).

According to a preferred aspect of at least one embodiment of the invention, the projection device is disposed at least partly on the first side arm and/or the second side arm. Light can therefore be projected onto the left and/or right side of the patient in a constructionally simple manner.

According to a preferred aspect of at least one embodiment of the invention, the frame element has an illumination device for generating at least one light signal. The illumination device can have e.g. a light source incorporated in the frame element. The light signal provides enhanced patient communication, particularly information or a patient instruction. For example, the light intensity can be modulated in order to indicate a breathing rate to the patient. The color of the light can indicate to the patient, for example, the current operating state of the equipment (e.g. waiting, scan impending, scan running) and/or the patient behavior required (e.g. small movements non-critical, stop moving, hold breath). In particular, one or more light elements for generating light, e.g. organic light-emitting diodes, can be disposed along the frame element in the form of a halo, for example. This enables an illumination device having improved visibility to be implemented.

According to a preferred aspect of at least one embodiment of the invention, the medical imaging device has another frame element for disposing at least one other component relative to the imaging area and/or the patient positioning device, wherein the other frame element has another first side arm, another second side arm and another apex area disposed between the other first side arm and the other second side arm, wherein the apex area is disposed or can be disposed in front of the imaging area in respect of the longitudinal direction and the other apex area is disposed or can be disposed behind the imaging area in respect of the longitudinal direction.

According to at least one embodiment of the invention, the other frame element can have one or more of the features of the frame element. The at least one other component can have one or more of the features of the at least one component.

In particular, the medical imaging device can have another first mounting device and another second mounting device for retaining the other frame element. The other first mounting device and the other second mounting device can have one or more of the features of the first and the second mounting device.

In particular, the frame element can be disposed in a front area and the other frame element in a rear area of the medical imaging device. This avoids swivel mounting and movement of the frame element. As a result, the mechanical stability of the frame element is increased. A 3D camera, for example, for patient positioning via positioning algorithms can be disposed on the frame element. Another camera for patient monitoring can be disposed on the other frame element. A monitor visible to the patient can be disposed both on the frame element and on the other frame element.

According to a preferred aspect of at least one embodiment of the invention, the frame element and the other frame element together form another circumferentially closed shape. In particular, the other circumferentially closed shape can be annular. The other circumferentially closed shape possesses high strength and rigidity. A mechanically particularly stable disposition of the at least one component and of the at least one other component can therefore be achieved. In particular, the other circumferentially closed shape can be retained between the first and the second mounting device. This obviates the need for additional mounting devices for retaining the other frame element.

According to a preferred aspect of at least one embodiment of the invention, the medical imaging device is selected from the group comprising a computed tomography device (CT scanner), a single photon emission computed tomography device (SPECT scanner), a positron emission tomography device (PET scanner), a magnetic resonance tomography scanner and combinations thereof. In particular, the medical imaging device can be a PET/CT scanner or a SPECT/CT scanner. In particular, the medical imaging device can have an X-ray device, a C-arm X-ray device, an ultrasound device or the like. The medical imaging device can also have a combination of a plurality of imaging and/or irradiating modalities. An irradiating modality can have, for example, an irradiation device for therapeutic irradiation.

The imaging area can comprise in particular a spatial effective area in which an interaction between an object to be imaged and the medical imaging device can be implemented such that scan data suitable for the reconstruction of an image of the object in question by way of the medical imaging device can be generated.

Figure 1:
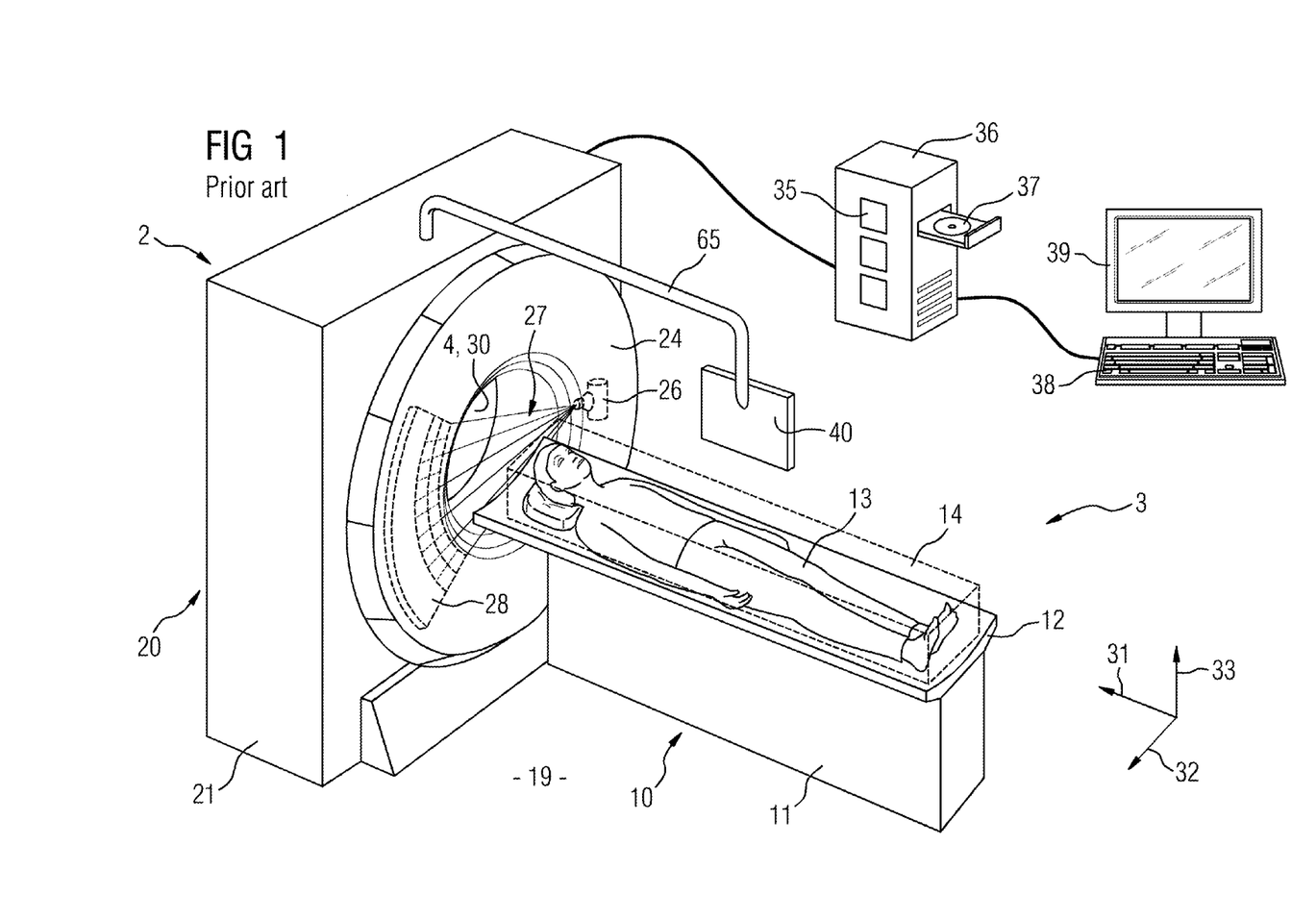
FIG. 1 shows a perspective view of an example of a medical imaging device having an imaging area formed by a tunnel-like aperture and having a patient positioning device.

FIG. 1 shows a perspective view of an example of a medical imaging device 2. In the example shown in FIG. 1, the medical imaging device 2 is, without limitation of the general inventive concept, a computed tomography device 2.

The medical imaging device 2 has a gantry 20. The gantry 20 has a stationary support frame 21. The gantry 20 has a rotor 24 rotatably mounted via a pivot bearing device. The rotor 24 is rotatably mounted about an axis of rotation essentially parallel to the longitudinal direction 31. Disposed on the rotor 24 is a radiation projection device 26, 28 for obtaining radiation projections of a region interest. The region of interest is disposed in an imaging area 4 formed by a tunnel-like aperture 30. The radiation projection device 26, 28 has a radiation source 26, e.g. an X-ray radiation source, and a radiation detector 28, e.g. an X-ray radiation detector. Radiation can be applied on a primary beam path 27 from the radiation source 26 to the region of interest and, after interaction with the region of interest, on to the radiation detector 28.

A tomographic image of the region of interest can be reconstructed on the basis of radiation projections which are obtained of the region of interest from different radiation projection directions by rotation of the radiation projection device 26, 28 around the tunnel-like aperture 30. To reconstruct a tomographic image, the medical imaging device 2 has an appropriately designed data processing unit 35.

The medical imaging device 2 has a control device 36 for controlling the medical imaging device 2. The control device 36 has a storage medium 37 on which computer programs for controlling the medical imaging device 2 are executably stored. The medical imaging device 2 also has an input unit 38 for entering control information, e.g. imaging parameters and examination parameters, and an output unit 39 for outputting control information and reconstructed images.

The medical imaging device 2 has an imaging area 4 formed by the tunnel-like aperture 30, and a patient positioning device 10. The patient positioning device 10 has a positioning table 11 and a transfer plate 12 for positioning a patient 13 in a patient positioning area 14. The transfer plate 12 is disposed on the positioning table 11 in a movable manner relative to the positioning table 11 such that the transfer plate 12 can be moved into the imaging area 4 in a longitudinal direction 31 of the transfer plate 12. The medical imaging device 2 has a support arm 65 and another input and output device 40 disposed on the support arm 65, wherein the other input and output device 40 is constituted by a touch-sensitive display.

Figure 2:
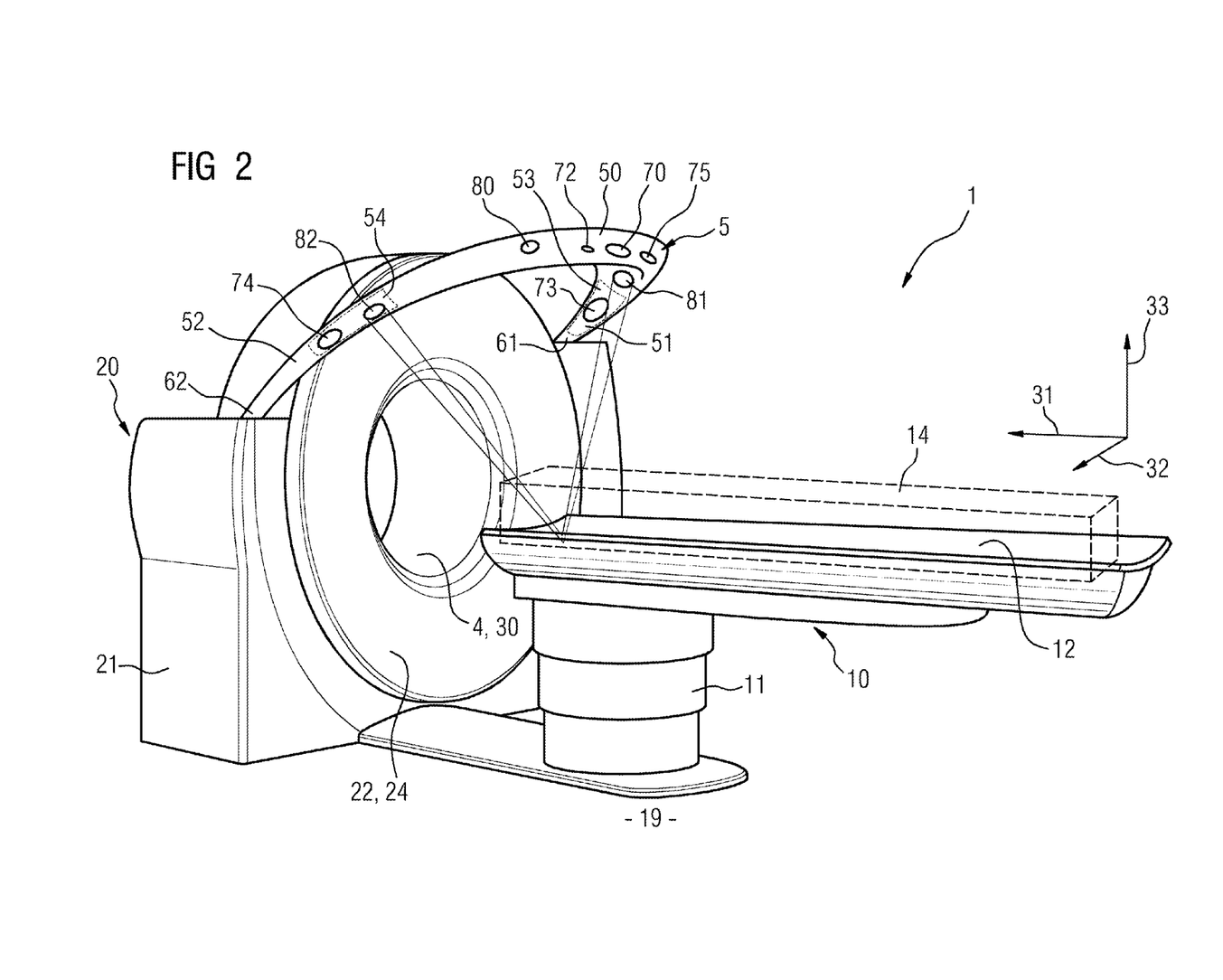
FIG. 2 shows a perspective view of a first example embodiment of a medical imaging device according to the invention.

FIG. 2 shows a perspective view of a first example embodiment of a medical imaging device 1 according to the invention. In FIG. 2 and the subsequent figures, the medical imaging device 1 is, without limitation of the general inventive concept, a computed tomography device 1. The medical imaging device 1 can have different above-described aspects of the example of a medical imaging device 2. The medical imaging device 1 according to the invention has a frame element 5 for disposing at least one component 64, 65, 70, 71, 72, 73, 74, 75, 76, 77, 78, 79, 81, 82, 86 of the medical imaging device 1 relative to the imaging area 4 and/or the patient positioning device 10, and a first mounting device 61 and a second mounting device 62 for retaining the frame element 5.

The frame element 5 has a first side arm 51, a second side arm 52 and an apex area 50 disposed between the first side arm 51 and the second side arm 52. The first mounting device 61 and the second mounting device 62 are disposed in a mutually offset manner in respect of a transverse direction 32 which is horizontal and at right angles to the longitudinal direction 31. The first mounting device 61 and the second mounting device 62 are disposed in a mutually offset manner in respect of a vertical direction 33. The apex area 50 is disposed approximately at the level of an upper edge of the gantry 20 in respect of the vertical direction 33.

The frame element 5 is retained in an offset manner between the first mounting device 61 and the second mounting device 62 such that the first side arm 51 is disposed between the apex area 50 and the first mounting device 61 and the second side arm 52 is disposed between the apex area 50 and the second mounting device 62. The apex area 50 is disposed in an area defined by the transfer plate 12 in respect of the transverse direction 32. The apex area 50 is disposed, in respect of the vertical direction 33, above a patient positioning area 14 provided above the transfer plate 12 for positioning the patient 13. At least one section 53 of the first side arm 51 and at least one section 54 of the second side arm 52 are disposed between the apex area 50 and the imaging area 4 in respect of the longitudinal direction 31. At least one section 53 of the first side arm 51 and at least one section 54 of the second side arm 52 are disposed between the apex area 50 and the gantry 20 in respect of the longitudinal direction 31. The apex area 50 is retained in an projecting manner 52 along the longitudinal direction 31 between the first side arm 51 and the second side arm 52.

In respect of the transverse direction 32, the first side arm 51 is disposed to the left of the patient positioning area 14 and the second side arm 52 is disposed to the right of the patient positioning area 14. The left-hand side and right-hand side are defined with respect to a vertical plane running through the patient positioning area 14 in the longitudinal direction 31.

In respect of the longitudinal direction 31, the first mounting device 61 and the second mounting device 62 are disposed in an area defined by the imaging area 4. In respect of the transverse direction 32, the first mounting device 61 is disposed to the left of the patient positioning area 14 and the second mounting device 62 is disposed to the right of the patient positioning area 14. In particular, the first mounting device 61 is disposed to the left of the imaging area 4 and the second mounting device 62 is disposed to the right of the imaging area 4 in respect of the transverse direction 32.

The first side arm 51, the second side arm 52 and the apex area 50 together form a U-shaped section of the frame element 5. In particular, the frame element 5 is of curved design.

The first mounting device 61 and the second mounting device 62 are disposed on the gantry 20. The gantry 20 constitutes a supporting structure of the medical imaging device 1. In particular, the gantry 20 is suitable for absorbing forces and torques acting on the medical imaging device 1 and transmitting then to a structural support 19. Without limitation of the general inventive concept, in the present and in the following examples the structural support 19 is a floor 19 of the examination room in which the medical imaging device 1 is disposed. In particular, cables which can transmit data and/or power to and from the at least one component 64, 65, 70, 71, 72, 73, 74, 75, 76, 77, 78, 79, 81, 82, 86 are run from the gantry 20 to the frame element 5. In particular, the first mounting device 61 is disposed on a left-hand side of the gantry 20 and the second mounting device 62 on a right-hand side of the gantry 20. The frame element 5 therefore extends from the left-hand side of the gantry 20 to the right-hand side of the gantry 20. The frame element 5 is therefore supported by the left- and right-hand side of the gantry 20.

The gantry 20 has tilting frame 22 tiltably mounted on the stationary support frame 21. The tilting frame 22 is tiltable about a tilt axis essentially parallel to the transverse direction 32. The first mounting device 61 and the second mounting device 62 are disposed on the stationary support frame 21. The frame element 5 is disposed on the stationary support frame 21 in such a way that the tilting frame 22 is prevented from colliding with the frame element 5. The tilting frame 22 enables the rotor 24 to be tilted about an axis parallel to the transverse direction 32.

The frame element 5 and the gantry 20 together form a circumferentially closed shape.

The frame element 5 can optionally be movably retained between the first mounting device 61 and the second mounting device 62 such that the position of the apex area 50 can be adjusted in respect of the longitudinal direction 31 and/or in respect of the vertical direction 33. Optionally the frame element 5 is swivel mounted between the first mounting device 61 and the second mounting device 62. The frame element 5 is optionally swivel mounted between the first mounting device 61 and the second mounting device 62 from a front area to a rear area of the medical imaging device 1. The front area and the rear area are defined in relation to a vertical plane running through the imaging area 4 in the transverse direction 32. The positioning table 11 is disposed in front of the imaging area 4 in respect of the longitudinal direction 31.

In the apex area 50, at least one camera 70 is disposed such that the imaging area 4 and the patient positioning area 14 are optically capturable by the camera 70 at least partially. The patient 13 is therefore optically capturable both when the patient 13 on the transfer plate 12 is positioned in front of or behind the medical imaging device 1 and when the patient 13 has been moved into the imaging area 4. To improve the view into the imaging area 4, the camera 70 is therefore optionally disposed so as to be rotatable relative to the frame element 5 about an axis parallel to the transverse direction 32.

A microphone 72 and a plurality of loudspeakers 73, 74, 75 are disposed on the frame element 5. In particular, the microphone 72 is disposed in the apex area 50. In particular, a first loudspeaker 73 is disposed on the first side arm 51 and a second loudspeaker 74 on the second side arm 52.

Disposed on the frame element 5 is a projection device 81, 82 for projecting light into the imaging area 4 and into the patient positioning area 14. In particular, the projection device 81, 82 has a plurality of projection elements 81, 82. The projection elements 81, 82 are disposed at intervals in the longitudinal direction 31 and in the transverse direction 32 on the frame element 5. The region onto which light can be projected encompasses parts of the left-hand side and right-hand side of the patient 13. In particular, the light is a laser.

The medical imaging device 1 has a laser-based intervention system. The laser-based intervention system incorporates the projection device 81, 82. The laser-based intervention system also has a projection control unit for controlling the projection device 81, 82.

The projection device 81, 82 is disposed at least partly on the first side arm 51 and the second side arm 52. In particular, a first projection element 81 is disposed on the first side arm 51 and a second projection element 82 is disposed on the second side arm 52.

Figure 3:
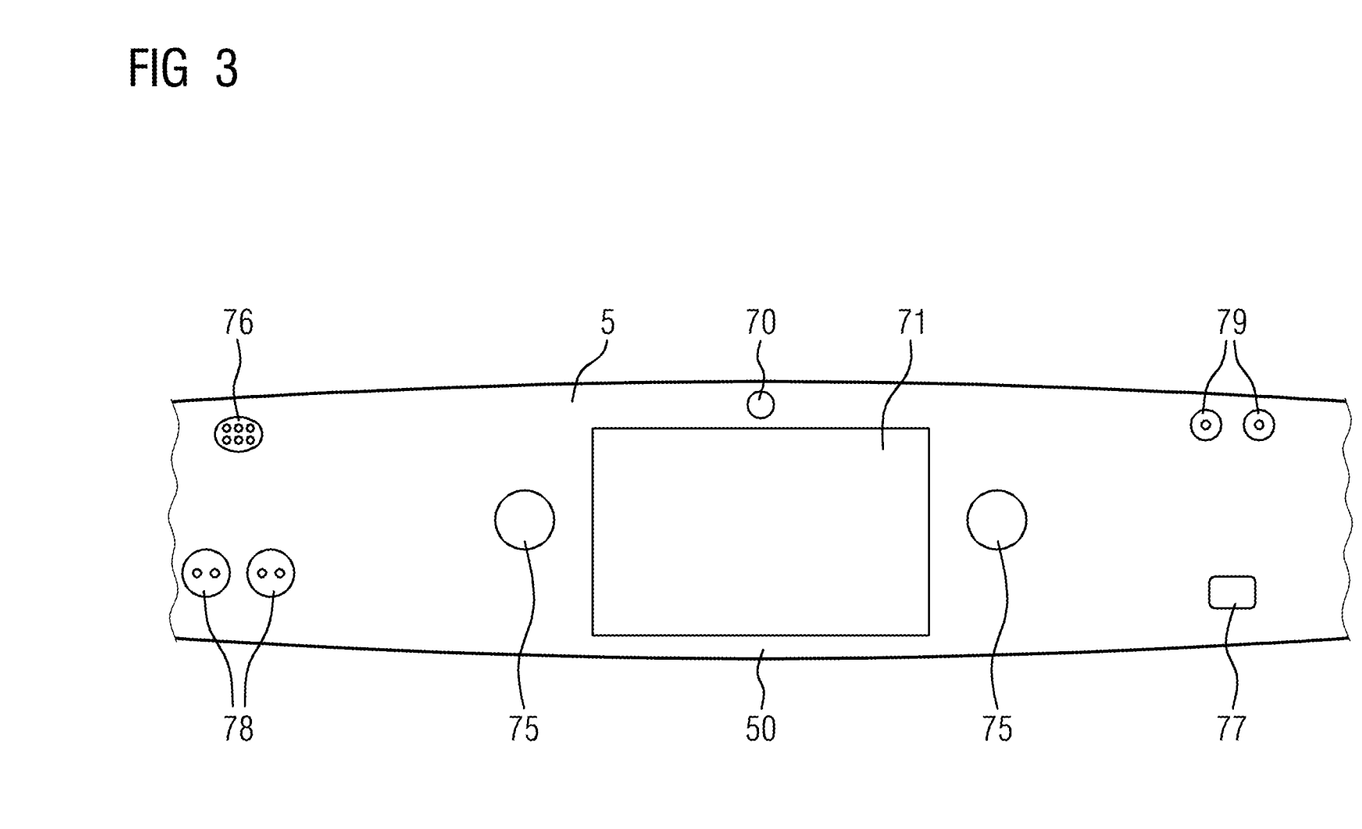
FIG. 3 shows a perspective view of a frame element of the medical imaging device shown in FIG. 2.

FIG. 3 shows a schematic partial view of the curved frame element 5 of the medical imaging device 1 shown in FIG. 2. In the apex area 50, a display device 71 is disposed such that the display device 71 is viewable from at least one part of the imaging area 4 and/or at least one part of the patient positioning area 14. To improve the visibility of the display device 71 for the patient 13, the display device 71 is optionally disposed so as to rotate relative to the frame element 5 about another axis parallel to the transverse direction 32.

A plurality of interfaces 76, 77, 78, 79 for transmitting data and/or power are disposed on the frame element 5. In particular, an interface 76 for connection to a device for physiological monitoring is disposed on the frame element 5. In particular, an interface 77 for connection to an injection device is disposed on the frame element 5. In particular, an interface 78 designed for connection to the electrical power supply of the at least one component 64, 65, 70, 71, 72, 73, 74, 75, 76, 77, 78, 79, 81, 82, 86 and/or of a device which can consume power and/or process data is disposed on the frame element 5. In particular, cables for transmitting data and/or power are incorporated in the frame element 5.

Figure 4:
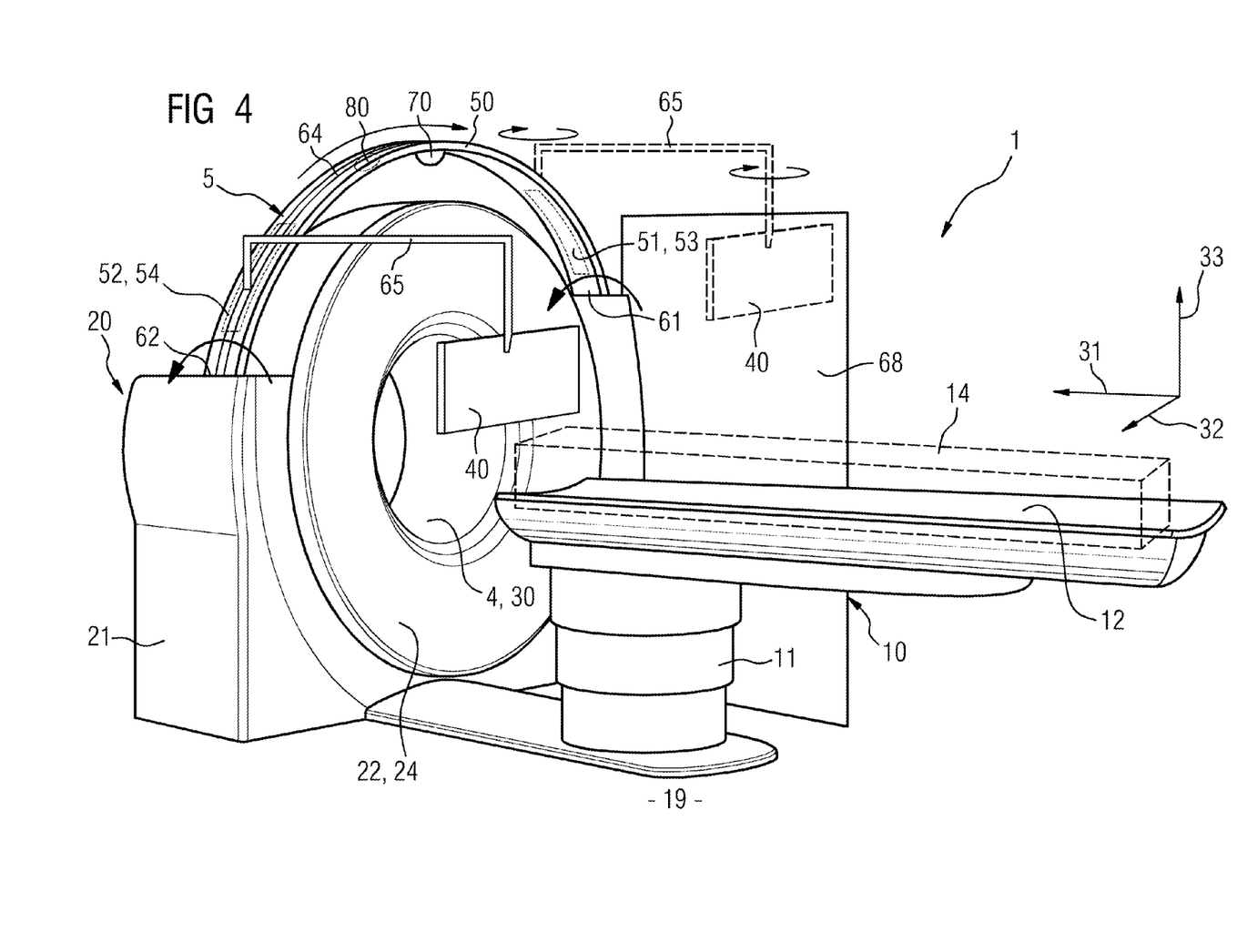
FIG. 4 shows a perspective view of a second example embodiment of a medical imaging device according to the invention.

FIG. 4 shows a perspective view of a second example embodiment of a medical imaging device according to the invention.

Here there is disposed on the frame element 5 a support arm 65 for disposing the at least one component 64, 65, 70, 71, 72, 73, 74, 75, 76, 77, 78, 79, 81, 82, 86. In particular, the support arm 65 is disposed on the frame element 5 so as to be able to rotate and swivel relative to the frame element 5. The support arm 65 can optionally have one or more articulations and/or one or more telescopic devices.

The frame element 5 has a device 64 for positioning the support arm 65 along the frame element 5. A guide rail 64 incorporated in the frame element 5 is provided for positioning the support arm along the frame element.

An input and/or output device 40 connected to the control device 36 of the medical imaging device 1 is disposed on the frame element 5. This connection can be hard-wired or wireless. The input and output device 40 is in particular rotatably disposed on a support arm 65 which can be positioned along the frame element 5, for example. In this example the input and output device 40 is constituted by a touchpad.

The medical imaging device 1 shown in FIG. 4 has a partition plate 68 for shielding against ionizing radiation. In particular, the input and output device 40 can be disposed in an area facing away from the imaging area 4 in respect of the partition plate 68 by way of the support arm 65 and the rail guide 64.

Figure 5:
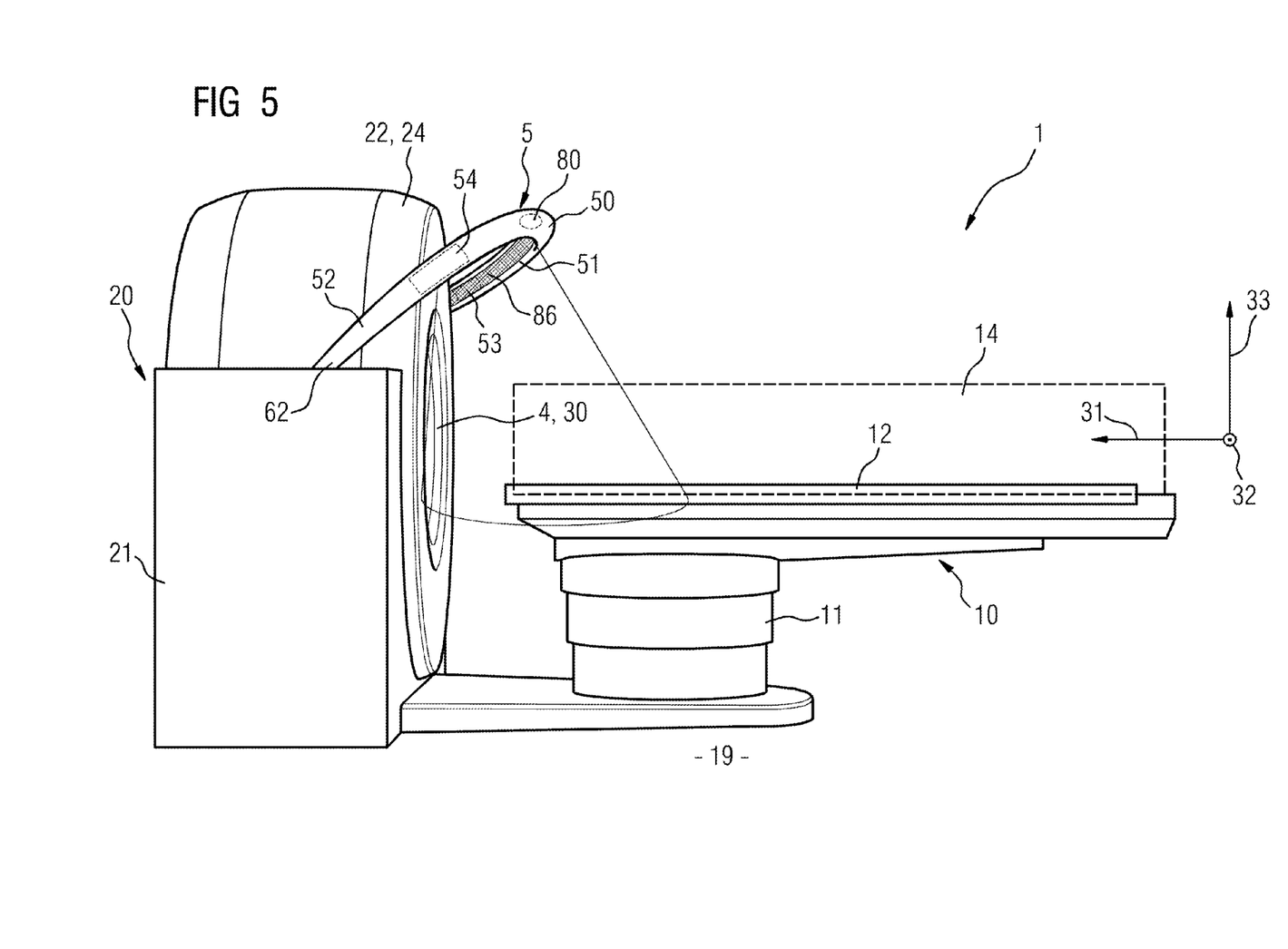
FIG. 5 shows a perspective view of a third example embodiment of a medical imaging device according to the invention.

FIG. 5 shows a perspective view of a third example embodiment of a medical imaging device according to the invention. Here the frame element 5 has an illumination device 86 for generating at least one light signal. The illumination device 86 has a light source incorporated in the frame element 5. The light signal is used in particular for enhanced patient communication, in particular to inform or instruct the patient 13. In particular, a plurality of light elements for generating light, e.g. organic light-emitting diodes, are disposed along the frame element 5 e.g. in the form of a halo.

Figure 6:
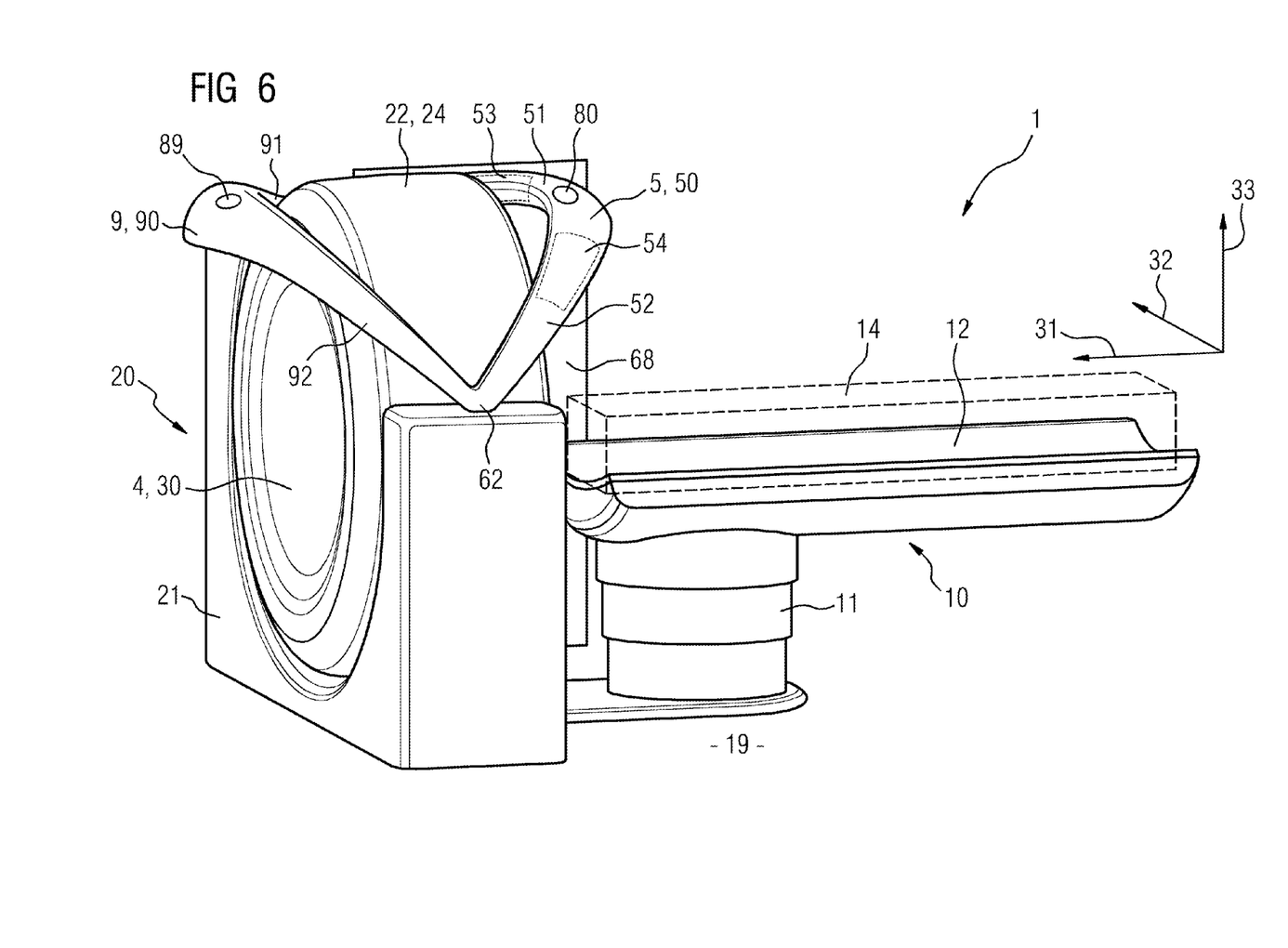
FIG. 6 shows a perspective view of a fourth example embodiment of a medical imaging device according to the invention.

FIG. 6 shows a perspective view of a fourth example embodiment of a medical imaging device according to the invention. Here the medical imaging device 1 has another frame element 9 for disposing at least one other component 89 relative to the imaging area 4 and/or the patient positioning device 10. The other frame element 9 has another first side arm 91, another second side arm 92 and another apex area 90 disposed between the other first side arm 91 and the other second side arm 92, wherein the apex area 50 is disposed in front of the imaging area 4 in respect of the longitudinal direction 31 and the other apex area 90 is disposed behind the imaging area 4 in respect of the longitudinal direction 31. In particular, the frame element 5 is disposed in a front area and the other element frame element 9 in a rear area of the medical imaging device 1. The other frame element 9 is retained between the first mounting device 61 and the second mounting device 62 in such a way that the other first side arm 91 is disposed between the other apex area 90 and the first mounting device 61, and the other second side arm 92 is disposed between the other apex area 90 and the second mounting device 62.

Figure 7:
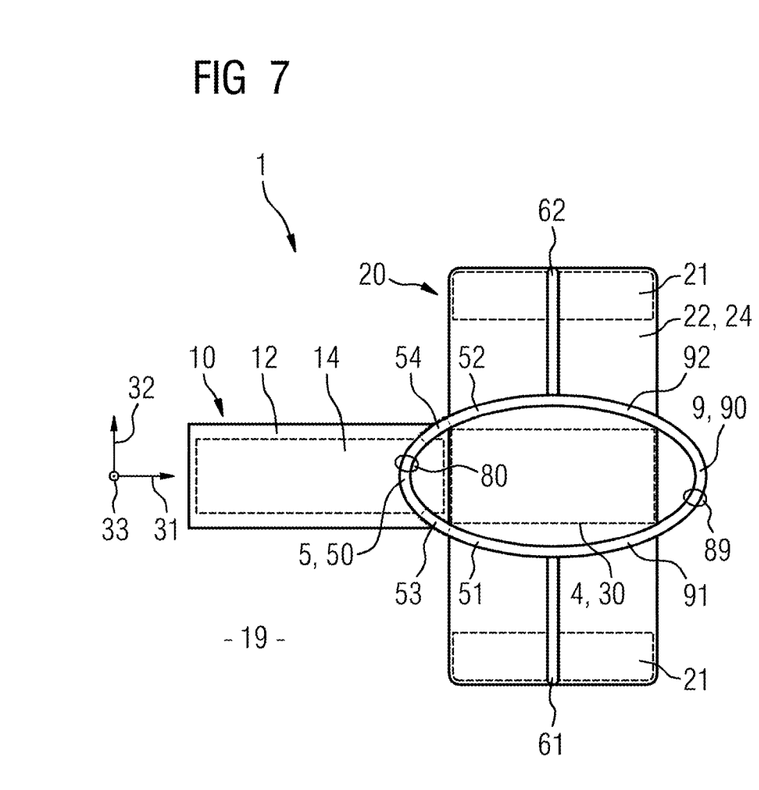
FIG. 7 shows a plan view of a fifth example embodiment of a medical imaging device according to the invention.

FIG. 7 shows a perspective view of a fifth example embodiment of the medical imaging device according to the invention. Here the frame element 5 and the other frame element 9 together form another circumferentially closed shape. In particular, the other circumferentially closed shape is annular. In particular, the other circumferentially closed shape is retained between the first mounting device 61 and second mounting device 62.

Figure 8:
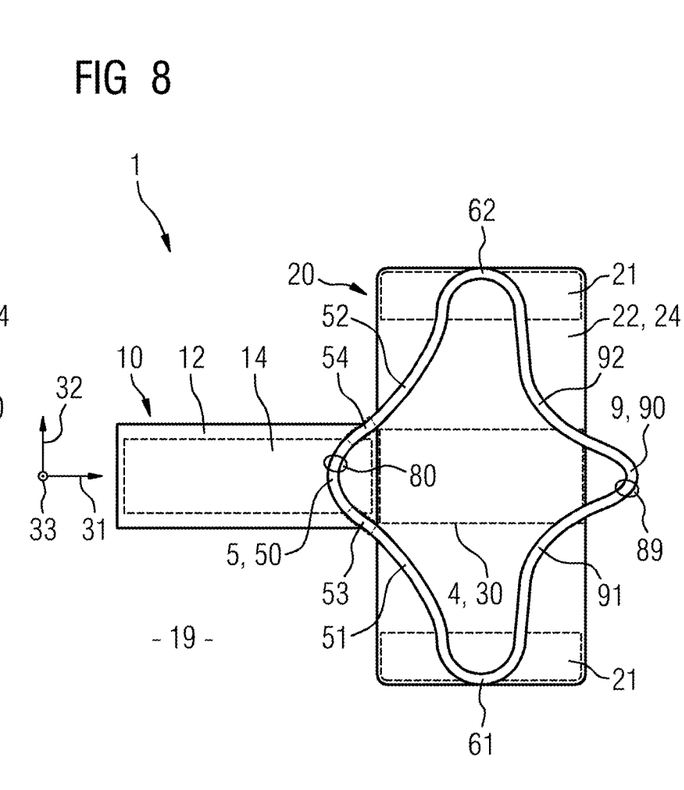
FIG. 8 shows a plan view of a sixth example embodiment of a medical imaging device according to the invention.

FIG. 8 shows a perspective view of a sixth example embodiment of a medical imaging device according to the invention. Here the frame element 5 and the other frame element 9 together form another circumferentially closed shape.

At least one embodiment of the invention therefore provides an improved disposition of at least one component relative to the imaging area and/or the patient positioning device of the medical imaging device.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Although the invention has been illustrated and described in detail by advantageous embodiments, the invention is not limited by the examples disclosed and other variations may be inferred therefrom by a person skilled in the art without departing from the scope of protection sought for the invention.

What is claimed is:

1. A medical imaging device, comprising:
   an imaging area;
   a patient positioning device including a positioning table and a transfer plate for positioning a patient in a patient positioning area;
   a frame element for disposing at least one component relative to at least one of the imaging area and the patient positioning device, wherein the frame element includes a first side arm, a second side arm and an apex area disposed between the first side arm and the second side arm, the apex area being disposed above the transfer plate in respect of a vertical direction;
   a first mounting device and a second mounting device for retaining the frame element; and
   a gantry, at least one of the first mounting device and the second mounting device being disposed on the gantry and the gantry including a stationary support frame and a tilting frame, wherein the tilting frame is mounted in a tiltable manner on the stationary support frame, and wherein at least one of the first mounting device and the second mounting device are disposed on the tilting frame.

2. The medical imaging device of claim 1, wherein the transfer plate is disposed on the positioning table in a movable manner relative to the positioning table, the transfer plate being movable into the imaging area in a longitudinal direction of the transfer plate.

3. The medical imaging device of claim 2, wherein the frame element is retained between the first mounting device and the second mounting device, the first side arm being disposed between the apex area and the first mounting device, and the second side arm being disposed between the apex area and the second mounting device, and wherein the apex area is disposed in a region defined by the transfer plate in respect of a transverse direction, horizontal and at right angles to a longitudinal direction of the transfer plate.

4. The medical imaging device of claim 3, wherein the frame element and the gantry together form a circumferentially closed shape.

5. The medical imaging device of claim 2, wherein the frame element and the gantry together form a circumferentially closed shape.

6. The medical imaging device of claim 1, wherein the frame element is retained between the first mounting device and the second mounting device, the first side arm being disposed between the apex area and the first mounting device, and the second side arm being disposed between the apex area and the second mounting device, and wherein the apex area is disposed in a region defined by the transfer plate in respect of a transverse direction, horizontal and at right angles to a longitudinal direction of the transfer plate.

7. The medical imaging device of claim 1, wherein at least one of the first mounting device and the second mounting device are disposed on the stationary support frame.

8. The medical imaging device of claim 7, wherein the frame element and the gantry together form a circumferentially closed shape.

9. The medical imaging device of claim 1, wherein the frame element and the gantry together form a circumferentially closed shape.

10. The medical imaging device of claim 1, wherein the frame element is retained in a movable manner between the first mounting device and the second mounting device, a position of the apex area being adjustable in respect of at least one of a longitudinal direction and a vertical direction.

11. The medical imaging device of claim 1, wherein the at least one component includes at least one of a camera, a projection device, an illumination device, a display device, an input device, an output device, a microphone, a loudspeaker, an interface for transmitting at least one of data and power, a rail guide, and a support arm.

12. The medical imaging device of claim 1, wherein at least one camera is disposed on the apex area, at least one of the imaging area and the patient positioning area being optically capturable at least partially by the at least one camera.

13. The medical imaging device of claim 1, wherein a display device is disposed on the apex area, the display device being viewable from at least one part of at least one of the imaging area and the patient positioning area.

14. The medical imaging device of claim 1, wherein a projection device, to project light into at least one of the imaging area and the patient positioning area, is disposed on the frame element.

15. The medical imaging device of claim 1, further comprising:
    another frame element for disposing at least one other component relative to at least one of the imaging area and the patient positioning device, wherein the another frame element includes another first side arm, another second side arm and another apex area disposed between the another first side arm and the another second side arm, and wherein the apex area and the another apex area are oppositely disposed or are oppositely disposable in respect of the imaging area in a longitudinal direction.

16. The medical imaging device of claim 15, wherein the frame element and the another frame element together form another circumferentially closed shape.

17. The medical imaging device of claim 1, wherein the medical imaging device includes at least one of a computed tomography device, a single photon emission computed tomography device, a positron emission tomography device, and a magnetic resonance tomography device.

* * * * *